United States Patent [19]

Redha

[11] Patent Number: 5,152,773
[45] Date of Patent: Oct. 6, 1992

[54] MEDICAL INSTRUMENT

[76] Inventor: Falah Redha, Schulzenrain 11A, CH-3042 Ortschwaben, Switzerland

[21] Appl. No.: 499,313
[22] PCT Filed: Sep. 7, 1989
[86] PCT No.: PCT/DE89/00581
  § 371 Date: Jul. 9, 1990
  § 102(e) Date: Jul. 9, 1990
[87] PCT Pub. No.: WO90/02523
  PCT Pub. Date: Mar. 22, 1990

[30] Foreign Application Priority Data
  Sep. 9, 1988 [DE] Fed. Rep. of Germany ....... 3830704

[51] Int. Cl.$^5$ ............................................. A61B 17/32
[52] U.S. Cl. ....................................... 606/159; 604/22
[58] Field of Search ........ 606/159, 160, 161, 167–171; 609/22, 19; 128/751, 753, 754, 755

[56] References Cited

U.S. PATENT DOCUMENTS

| | | | |
|---|---|---|---|
| 2,868,206 | 1/1959 | Stoesser | 606/159 |
| 3,230,949 | 1/1966 | Rodriguez-Olleros | 606/159 |
| 3,508,553 | 4/1970 | Kanbar | 606/159 |
| 3,764,427 | 10/1973 | Reimels | 606/159 X |
| 3,837,345 | 9/1974 | Matar | |
| 4,273,128 | 6/1981 | Lary | 606/159 |
| 4,493,321 | 1/1985 | Leather | 606/159 |
| 4,685,458 | 8/1987 | Leckrone | 606/159 X |
| 4,747,821 | 5/1988 | Kensey et al. | |
| 4,765,332 | 8/1988 | Fischell et al. | |
| 4,794,928 | 1/1989 | Kletschka | 128/344 |
| 4,842,579 | 6/1989 | Shiber | 604/22 |
| 4,952,215 | 8/1990 | Ouriel et al. | 606/159 |
| 4,957,482 | 9/1990 | Shiber | 604/22 |
| 5,026,383 | 6/1991 | Nobles | 606/159 |
| 5,047,041 | 9/1991 | Samuels | 606/159 |
| 5,049,154 | 9/1991 | Quadri | 606/159 |
| 5,061,240 | 10/1991 | Cherian | 604/96 |
| 5,074,871 | 12/1991 | Groshong | 606/170 |

FOREIGN PATENT DOCUMENTS

| | | |
|---|---|---|
| 0117519 | 2/1984 | European Pat. Off. . |
| 1909080 | 11/1964 | Fed. Rep. of Germany . |
| 7908610 | 3/1979 | Fed. Rep. of Germany . |
| 3320984 | 12/1984 | Fed. Rep. of Germany . |
| 3800777 | 7/1988 | Fed. Rep. of Germany . |
| 1585065 | 1/1970 | France . |
| 8800458 | 1/1988 | PCT Int'l Appl. . |
| 2044103 | 3/1979 | United Kingdom . |
| 8909029 | 10/1989 | World Int. Prop. O. .......... 606/159 |

Primary Examiner—C. Fred Rosenbaum
Assistant Examiner—Mark O. Polutta
Attorney, Agent, or Firm—Speckman & Pauley

[57] ABSTRACT

A medical instrument for insertion into human vessels for removing plaque deposits from the walls of arteries and/or veins. It is formulated of a partially hollow and, seen in cross section, circular body, which by the means of a controllable, withdraw cutting device, can be extracted from the vessel after performing its primary function of slicing away any plaque deposits from the artery or vein wall, and collecting them in a residue chamber for removal. The tangent of the angles of the cutting section is defined by the central axis of the hollow body and a tangential line intersecting the cutting section increases continuously as the point of intersection of the tangential line with the cutting section is moved in the direction of the cutting edges. The angle of the cutting edges are more than 10 degrees, but less than 90 degrees, from the axis of the hollow body.

30 Claims, 6 Drawing Sheets

MEDICAL INSTRUMENT

BACKGROUND OF THE INVENTION

This invention relates to a medical instrument for the removal of plaque deposits from the walls of arteries and/or veins which is a vessel insertable, partially hollow and to an extent having a circular body in section, that is a practical, withdrawable and directable device, for the elimination of plaques by slicing off portions with cutting edges.

Arteriosclerosis, a chronic progressive, degenerative disease, especially located on the inner surface of artery walls (Intima), is an illness occurring very frequently in our civilized world, most commonly during the second half of normal life spans. For example, about 90% of such cases are the cause of arterial blockage diseases and holds the leading place in causes of death statistics. Through penetration of the thrombocytes in the cell interspaces, followed by lipoid containing deposits, the inner most walls of the vessels develop, what is known as atheromas changes, which leads to the death of cells and, finally, expanding of the connecting tissue at this artery wall site (Sclerosis). Through these changes the artery wall will lose its normal elasticity. Focal deposits, especially Cholesterin crystals that also penetrate to the middle of the vessel wall, lead to inflammatory reaction and more cell deaths. This results in calcium deposits, which cause growths in the vessel lumen, later attracting thrombosis.

There are cases wherein arteriosclerosis can be treated with medicines, dilating the vessel to increase the flow of blood. There exist some physio-therapeutic facilities that lead to improved circulation, in addition to which, some surgical procedures have been developed to treat arteriosclerosis. The surgical treatment of arteriosclerosis changes when particular organs or parts of the body are utilized. Vascular surgery can be successfully applied, especially in the following cases:

a) Arteriosclerosis alteration to the carotid artery that supplies blood to the brain.

b) Arteriosclerosis alteration to the coronary arteries: Coronary bypass and implanting, Arteria Thoracica Interna.

c) Serious arteriosclerosis disturbs the supply of blood to the extremities.

d) Arteriosclerosis to the kidney arteries.

e) The removal of Aneurysms.

Generally, with arteriosclerosis change, the following surgical techniques are applied:

a) The method of bypass, during which the closed artery is replaced by a section of the patient's vein or artery, or, synthetic material in the format of a vessel, to bridge the flow of blood into certain areas.

b) Edarteriaoectomy.

c) Implanting of a patch after endarteriaoectomy.

d) Implanting of a vessel prothesis, either as a replacement or bypass for the arteriosclerosis artery.

e) Sympathectomy.

f) Removing arteriosclerosis changes by the means of a balloon catheter.

As is known, arteriosclerosis changes are located mainly on internal walls of arteries, while the external walls remain relatively normal. When inner sclerotic material is removed or sliced from the internal wall, the surface is left smooth. For example, this can be performed with an instrument, such as is described in U.S. Pat. No. 4,765,332. This acknowledged instrument contains a somewhat basic cylindrical format with a pull-back cutting section that is also of cylindrical shape. The sharp edges of the cutting section are directed from the inside to the outside of the body which could lead to the injury of healthy vessels.

SUMMARY OF INVENTION

With regard to the foregoing technique, one object of this invention is to provide a medical instrument, with which asymmetric deposits can also be removed from the vessel wall without difficulty, safely preserving the vessel wall from damage. The major feature of this instrument is that the tangents of the angle defined by the intersection of the central axis of the main body and a tangential line from the cutting section, continually increases as the intersection of the tangential line with the cutting section is moved in the direction of the cutting edges, and the cutting edge is set such that the angle defined by the central axis of the main body and the tangential line from the cutting section is more than 10 degrees, but, less than 90 degrees.

A body such as this can be introduced into a vessel, enclosed in a catheter, to the desired location by using a contrast medium. The cutting edges of the device are disposed at the withdrawal end of the body facing the catheter and thus facing the point of insertion into the vessel. The catheter and the body are positioned in such a way that the plaque lays between the catheter and the body. Following this, the withdrawal device can be set in motion pulling the body toward the catheter and the selected section sliced off. The body may also be rotated, creating a saw-like action as it is pulled toward the catheter. This procedure can be repeated as many times as required until a smooth inner wall is achieved. When shaving the deposits, any residue is either retained within the body, or, can be removed by some means of suction.

A particularly practical feature of this invention is that the withdraw cable of the cutting section is surrounded by the hollow body and is securely connected to the face side of the hollow body.

The advantage of this arrangement is that, when slicing off residue, it can be contained within the body of the instrument, and then withdrawn from the vessel, after which, the hollow body can be replaced by another type. Within the scope of this invention, it is especially practical to have the hollow body in the form of polished bead, or, hollow cylinder with a convex face. Above all, through this arrangement, an insertion of a hollow body into a vessel is simplified, as the front face side of the body is tapered, thus allowing the blood to be more efficiently displaced.

With operation of this apparatus the other face side having the cutting edges comes into contact with the deposited plaques, and the operator, by manipulating the free end of the apparatus, expands the cutting edges to enable the slicing procedure to begin for removal of the plaque deposit. The convexity of the face side of the cutting section is of significance, as this avoids any injury to healthy tissue of the artery wall. Only the radial projecting plaque will be sliced away by the cutting action and the residue then extracted.

A further practical application is present, in that the hollow body, being of at least two shell shaped parts, can be expanded when used in the withdrawal direction. The volume of the hollow body can be enlarged and held together by the means of an expanding device.

The end of the withdrawal device, which faces the hollow body, is fitting with a threaded part for screwing onto the expansion device.

The expanding device of elasticated mouldable material has a central, coaxial threaded bore with the protruding end of the partially threaded cone being helmeted to cover the rear end of the hollow body. The complimentary helmet makes close contact with the rear end of the body. By these means, a medical instrument is exhibited that is not only adaptable to the narrow vessels, but also, to those of a much larger diameter.

The essentially cylindrical section of the hollow body is pressed against the internal wall of the artery, allowing the cutting edge of the apparatus to dislodge the plaque residue.

An additional advantage of this invention is that its hollow body is axially symmetric.

When particularly hard plaque is encountered, the hollow body can be replaced with one containing a zig-zag corrugated cutting edge. Through its saw-like application this cutting edge can quickly and easily remove any hard deposits of plaque.

A further advantage of this invention is that an end of the withdrawable cable is firmly attached to the appropriate end of the expanding device of the hollow body. This causes the sections of the body to separate and press against the wall of the artery. Relative to this is the size and format of the expansion device which can be applied to the internal walls of the follow body (conal, pyramidal, global, etc.) to enable its cutting function to have sufficient pressure against the plaque.

BRIEF DESCRIPTION OF THE DRAWINGS

For closer examination, embodiments of the applications of the instrument are schematically described in the following diagrams.

DESCRIPTION OF PREFERRED EMBODIMENTS

In FIGS. 1–4, as in FIGS. 7–11, the medical instruments shown are for the purpose of removing plaque deposits from artery walls.

Figure 5:
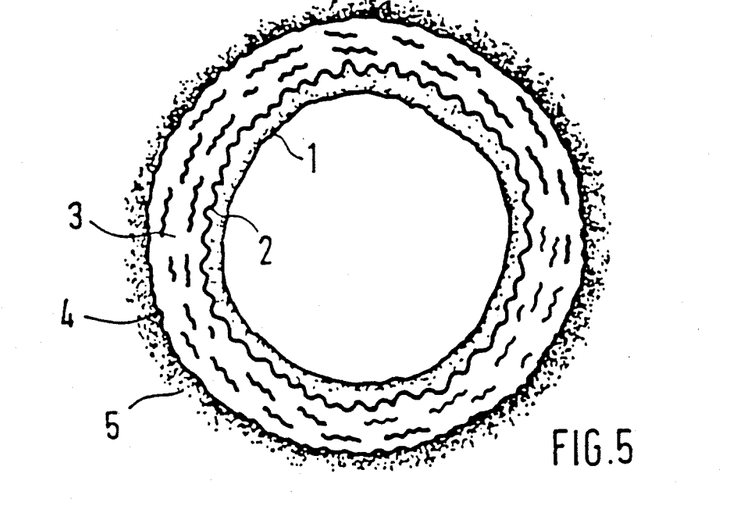
FIG. 5 is a cross-sectional view of a healthy artery wall.
Figure 6:
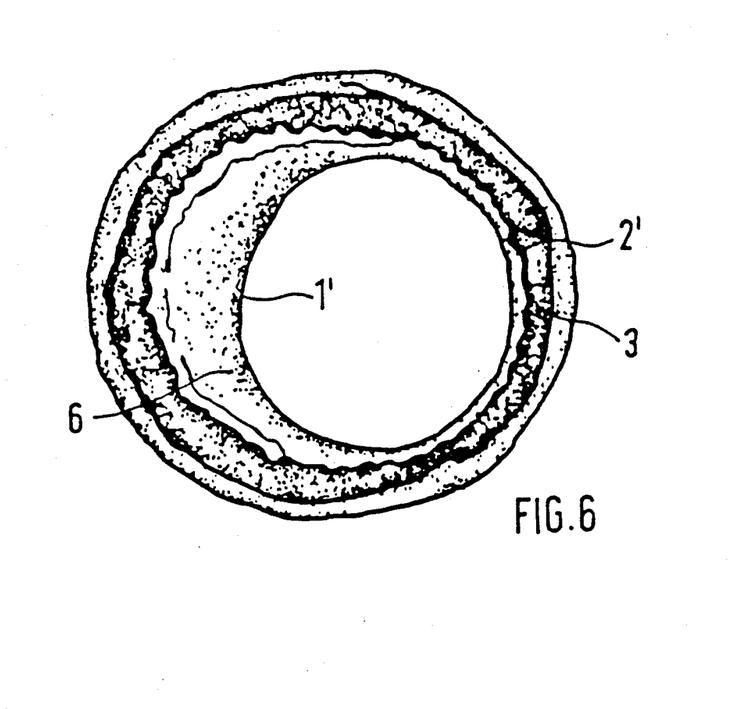
FIG. 6 is a cross-sectional view of an artery wall with arteriosclerosis.
Figure 7:
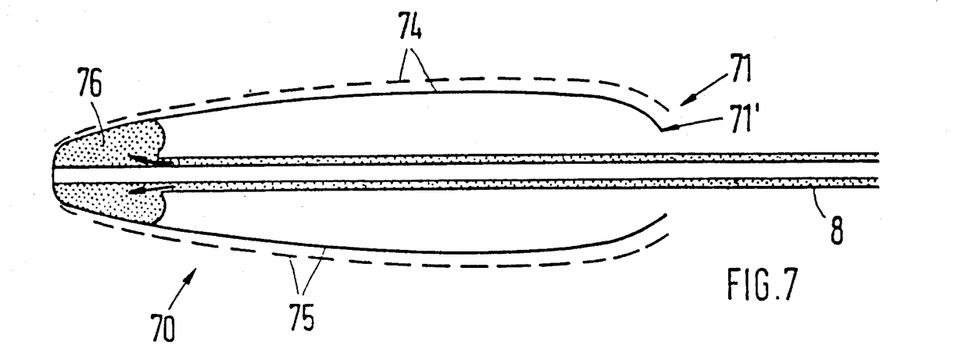
FIG. 7 is a partial cross-sectional view of a medical instrument having a pressure adjustable expansion body, according to one embodiment of this invention.
Figure 8:
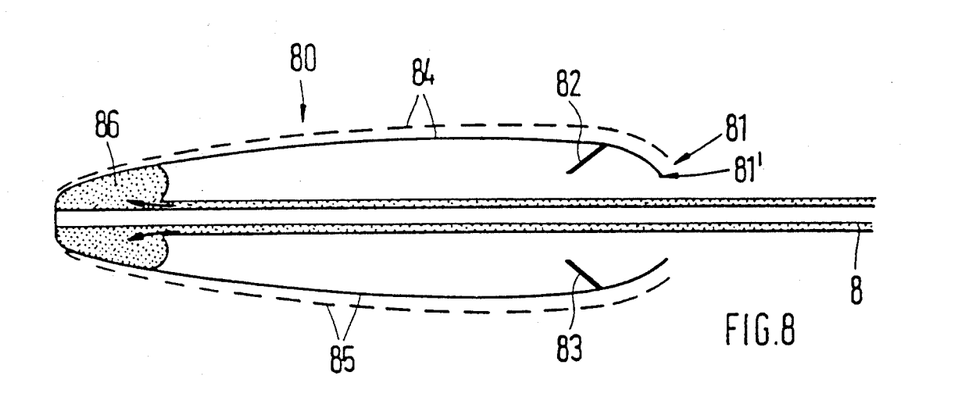
FIG. 8 is a medical instrument, as shown in FIG. 7, with a blockage body.

FIG. 5 shows a specific cross section of a healthy artery wall, while FIG. 6 shows a cross section of an artery with arteriosclerosis. The healthy artery wall (FIG. 5) consists of an Intima 1, and Elastica Interna 2, a Media 3, an Elastica Externa 4 and an Adventitia 5.

With an artery wall having arteriosclerosis (FIG. 6) Intima 1', with connective tissue is thickened. It is likewise with the Elastica Interna 2'. Between the Elastica Interna 2' and the Intima 1' there can be found a metrotic Intim pocket containing Cholesterol 6.

The medical instrument shown in FIGS. 1–4 is specifically for the insertion of a body (10, 20, 30, 40) into arteries. It includes a withdraw cable (8), which is also the directional drawing control cable for the slicing off of plaque deposit by using the cutting edges (11, 21, 31, 41).

It can be seen that the bodies (10, 20, 30, 40) are hollow bodies, having a plaque deposit cutting section (11, 21, 31, 41), in the area of the withdraw direction 9, the withdraw cable 8, can be formed of a thin tube that is securely connected through the cutting section (11, 21, 31, 41) that surrounds the other face side (12, 22, 32, 42) of the specified body. Generally, the hollow body, (10, 20, 30, 40) has the form of a polished bead, or hollow cylinder with convex face sides. In all cases, the cutting section (11, 21, 31 41) and the withdraw cable (8) are arranged so that no injury to the artery can occur. With the medical instrument shown in FIG. 1, the withdraw cable (8) is connected to the face side (12) by the means of an adhesive, or welding.

Figure 3:
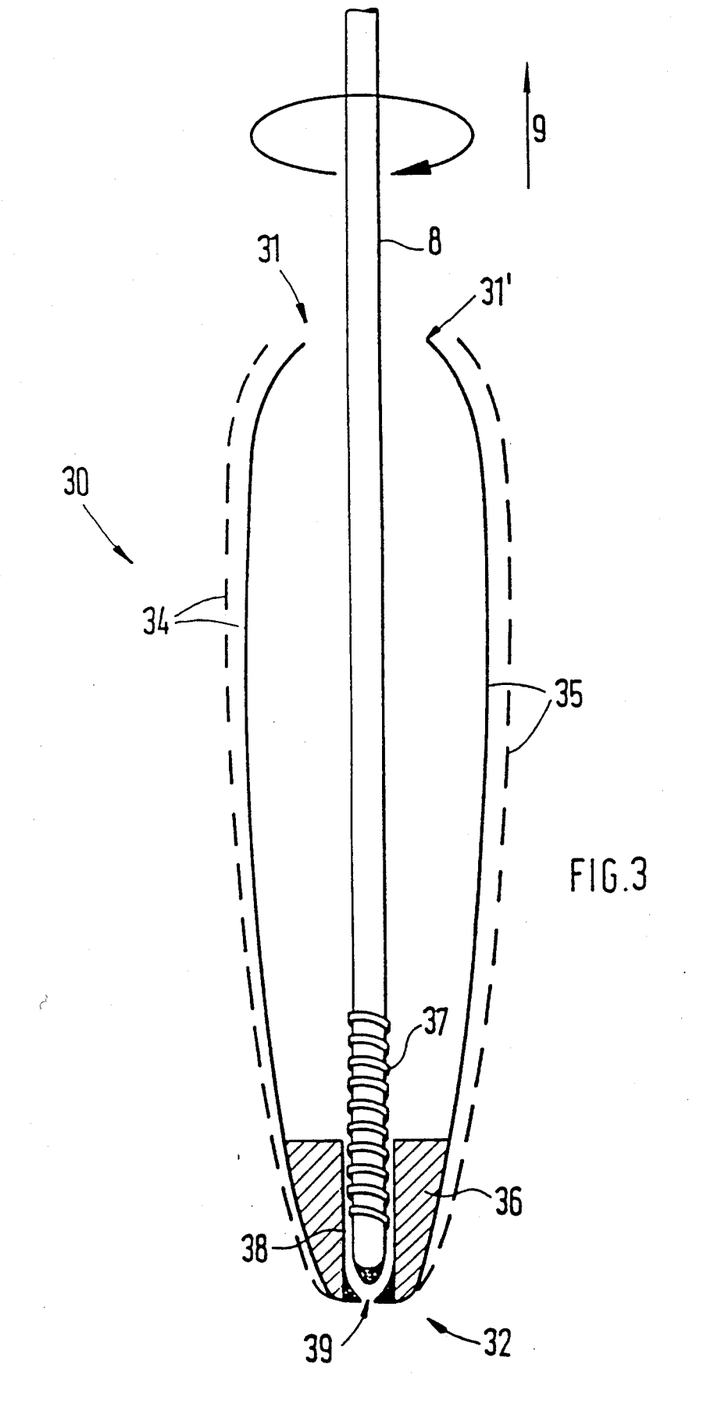
FIG. 3 is a partial cross-sectional view of a medical instrument according to another embodiment of this invention.
Figure 4:
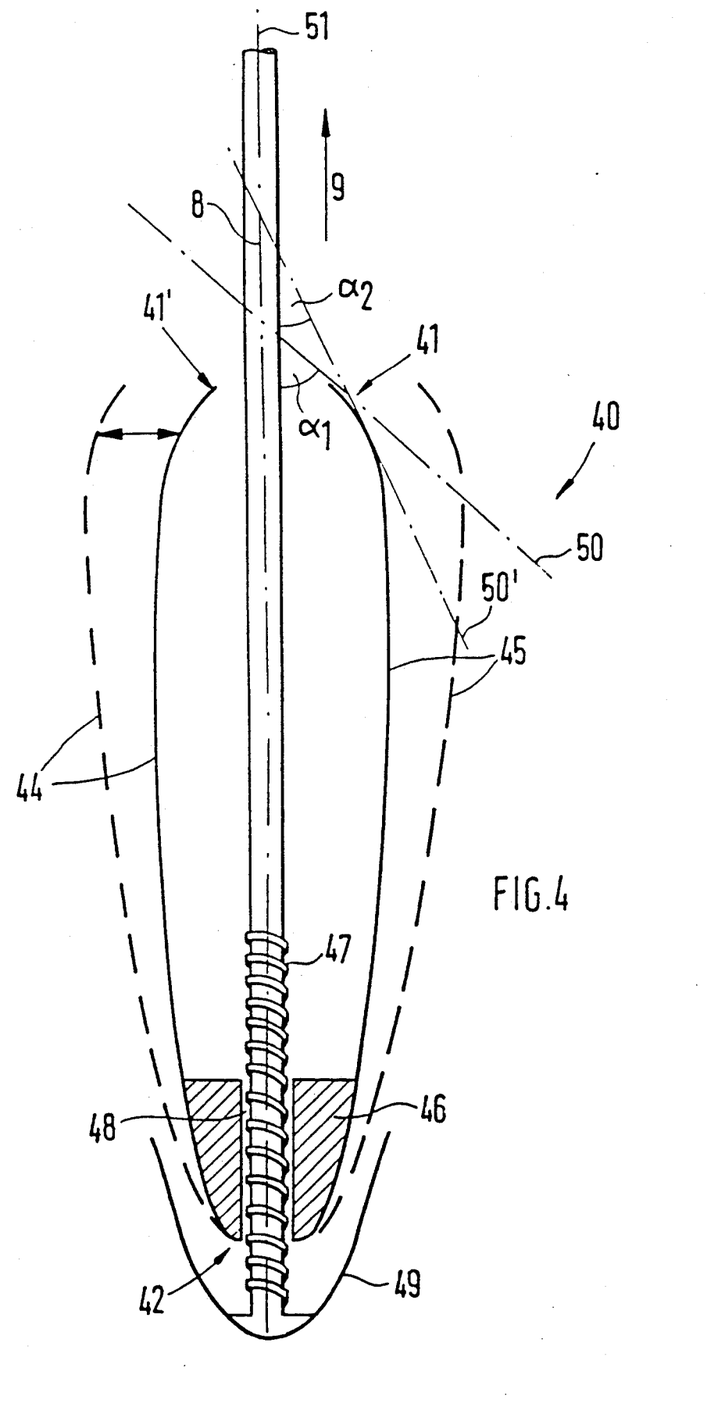
FIG. 4 is a partial cross-sectional view of a medical instrument according to yet another embodiment of this invention.

With this medical instrument, according to FIGS. 3 and 4, a specific hollow body (30, 40) is formed of two shell-shaped sections which, in its withdraw direction (9), are expandable, with these expandable shells of the body (34, 35, 44, 45) being retained by the expanding device (36, 46). The connecting end of the withdraw cable (8) is threaded to enable connection to the expanding device (36, 46)

With this medical instrument, according to FIG. 3, the expanding device (36) is formulated of elastic mouldable material and has a central, coaxial threaded bore (38), into which a partially threaded cone can be screwed. The outward facing end (39), of the bore (38), is narrowed, so that when the threaded end of the withdraw cable (8), is screwed to the end (39) of the bore (38), the end (39) expands so that the volume of the body (30) changes.

In FIG. 4 it can be seen that the expanding device (46) is made of elastic mouldable material and has a central, coaxial threaded bore (48). The protruding end, which is a partially threaded cone, has a complimentary helmet (49) facing towards the end of the hollow body (40), with which the helmet (49) makes close contact. The hollow body (10, 20, 30, 40, 70, 80, 90, 100) is axially symmetric. The tangent (50, 50') of the cutting section (41) forms, with the central axis (51) of the hollow body (40) angles $\alpha_1$ and $\alpha_2$ which are less than 90 degrees and more than 10 degrees. The cutting edges (11', 21', 31', 41') can be of a zig-zag or corrugated profile.

Figure 1:
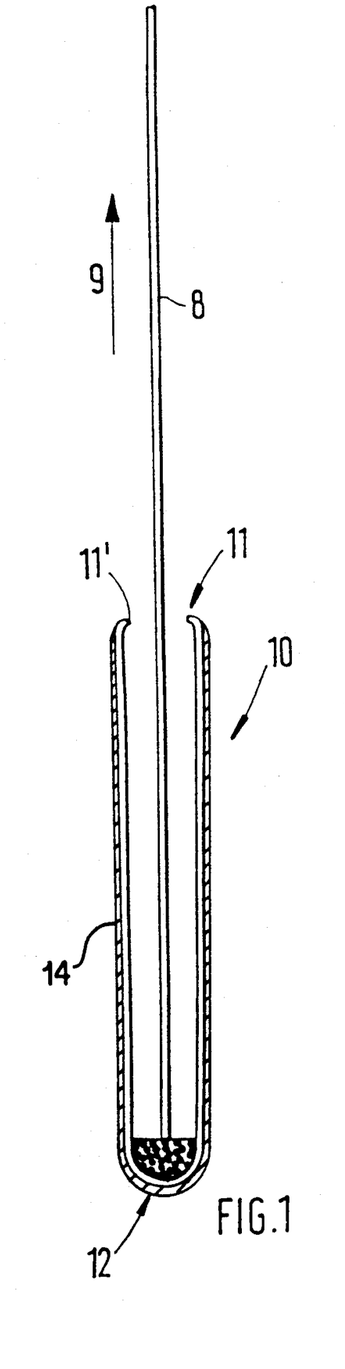
FIG. 1 is a partial cross-sectional view of a medical instrument according to one embodiment of this invention.
Figure 2:
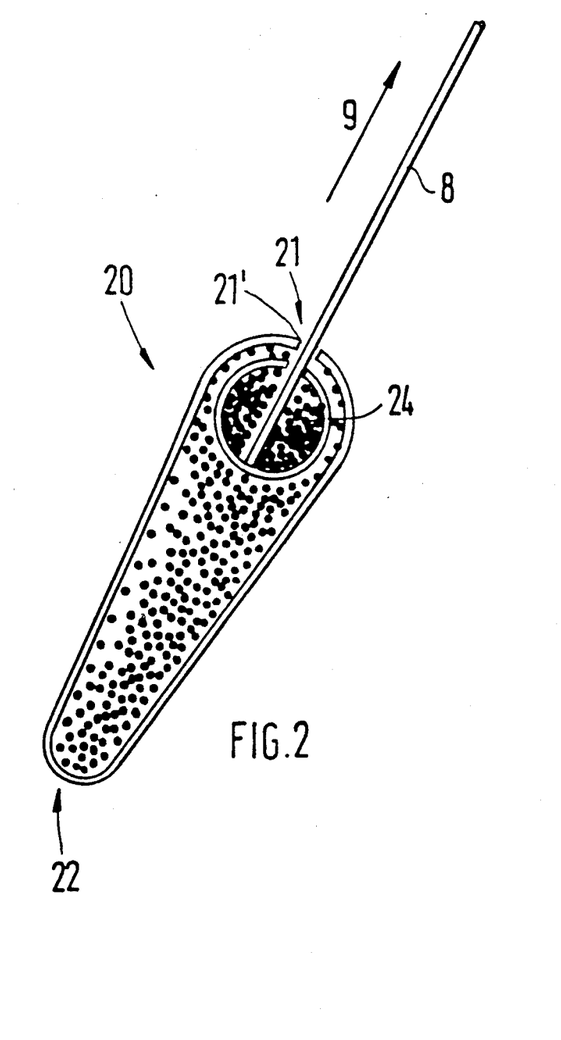
FIG. 2 is a partial cross-sectional view of a medical instrument according to another embodiment of this invention.

FIG. 2 shows the withdraw device (8) which lays within the hollow body (20) of the instrument and is also connected to the hollow body (20) by the adjustable expander (24), which in turn exerts pressure on parts of the hollow body (20), forcing them apart and against the artery wall. The hollow body (10, 20, 30, 40) can be manufactured from rust-free steel or another suitable material, or even a synthetic material.

In FIGS. 7 to 11, the body (70, 80, 90, 100, 110), with the cutting section (71, 81, 91, 101, 111), is illustrated with its sharp cutting edges (71', 81', 91', 101',111',). The elastic, mouldable expanding device is connected to the withdraw device (8) and this, in turn, is connected to the clamping device (76, 86, 96, 106, 116). The withdraw device (8) can be made of a tube or a double lumen tube, so that fluid or gas can be transmitted for adjusting the size of the expanding device (76, 86, 96, 106, 116). In the initial stage, the parts (74, 75, 84, 85, 94, 95, 104, 105, 114, 115) of the hollow body are at their narrowest when seen as a solid line in the drawings and, when the pressure medium is applied, the circumference of the expanded hollow body, which is then seen as a broken line on the drawings, increases, causing it to be pressed against the internal wall of the vessel.

FIGS. 8 to 11 show that the internal surface of the body (84, 94, 104, 105) with its blockage device (82, 83, 92, 93, 102, 103, 112, 113) retains within the body the residue of the plaque slicing.

Figure 9:
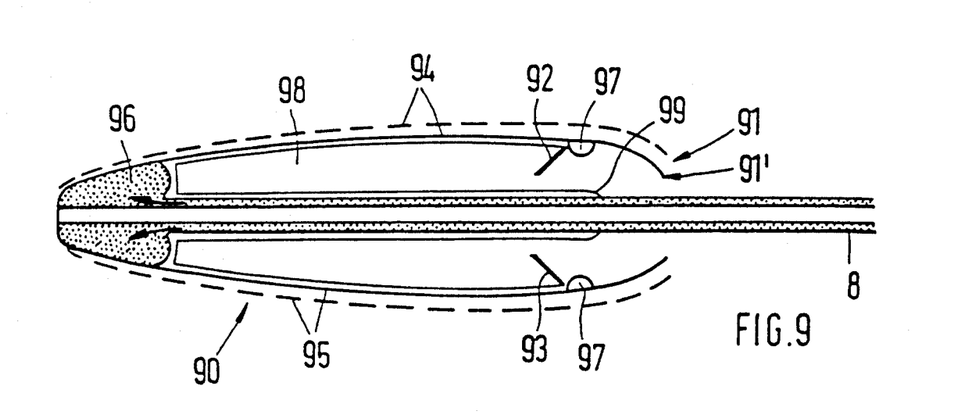
FIG. 9 is a medical instrument, as shown in FIG. 7, with another type of blockage body.

In FIG. 9, it can be seen that the residue retaining chamber (98), which surrounds the withdraw device (8), includes the blockage device (92, 93) which is retained by the projection (97) on the internal face of the hollow body. The blockage plates are projecting inwards so that the residue is securely retained in the chamber between the withdraw device (8) and the wall of the hollow body.

Figure 10:
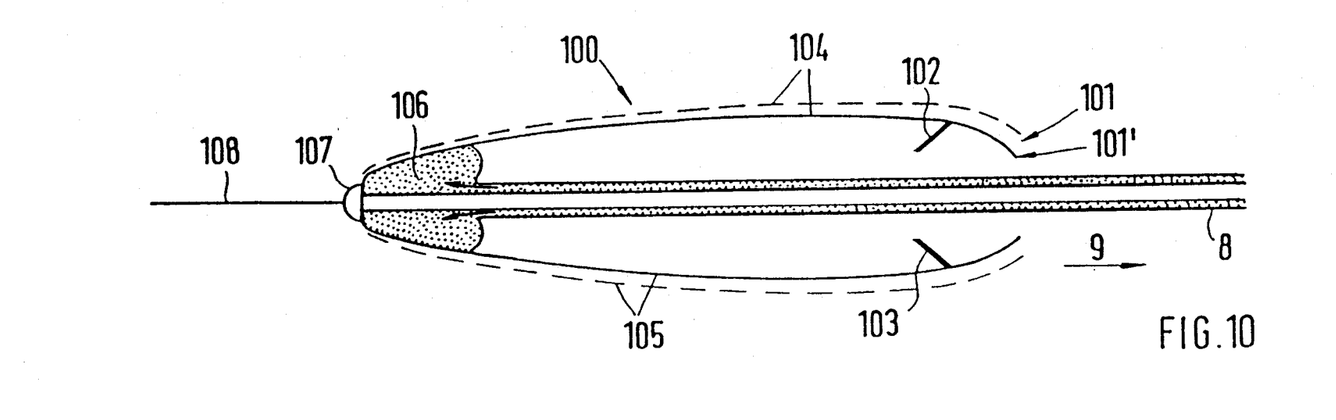
FIG. 10 is a medical instrument, as shown in FIG. 7, with a guiding catheter.

FIG. 10 shows a guide wire (108) connected to the body (100) and projecting through the sealing helmet (107).

Figure 11:
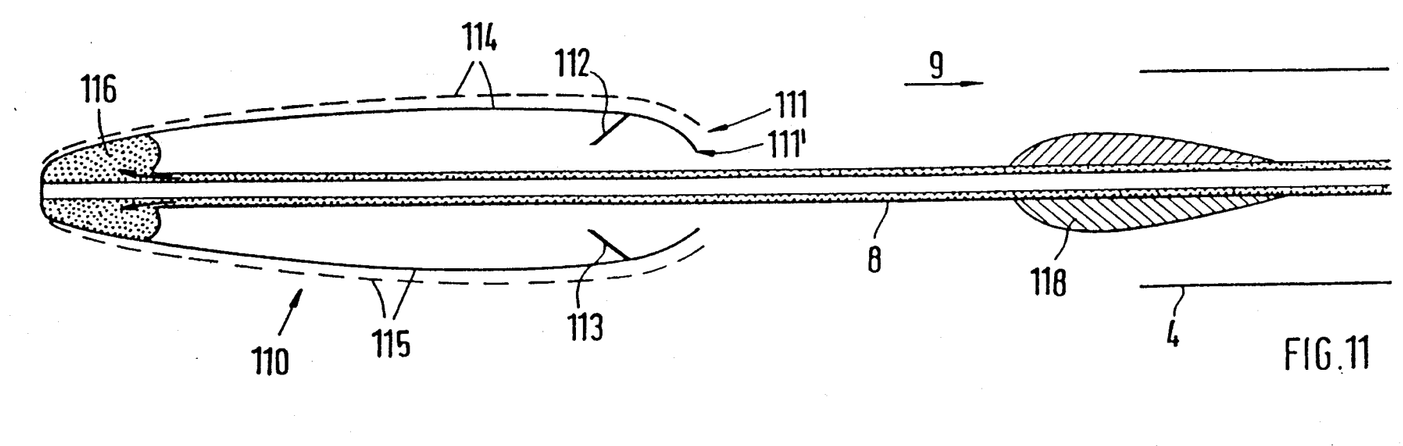
FIG. 11 is a medical instrument, as shown in FIG. 7, having a guiding body.

FIG. 11 shows a bulbous guide mounted on the withdraw device (8), in front of the cutting edge (111) of the body (100), which serves to guide the body of the instrument into the catheter opening.

The hollow body, with its withdraw device (8), can be manufactured of metal, which may be covered with an insulation material 14 for conducting electrical current, so as to enable the application of a powered cutting device. The cutting edges must be left bare for the function of cutting away plaque deposits.

I claim:

1. A medical device for removal of deposits from arterial and venous walls comprising: a body insertable within vessels, said body essentially circular in cross section, partially hollow, and having an insertion end and a withdrawal end, an elongated withdrawal device (8) attached within said body and extending from said withdrawal end of said body, a cutting element at said withdrawal end of said body, said cutting element having a convex surface facing away from said body and forming a cutting edge (41') whereby a tangential line (50', 50) intersecting a point of said convex surface and a central axis (51) of said body (40) forms an angle between said tangential line (50', 50) and said central axis (51), the tangent of which increases continuously as said tangential line (50', 50) intersects said convex surface of said cutting element continuously closer to said cutting edge (41'), said angel being greater than about 10 degrees and less than about 90 degrees when said tangential line (50', 50) intersects said convex surface at said cutting edge; and said body (10, 20, 30, 40, 70, 80, 90, 100, 110) further comprising at least two shell shaped parts (34, 35; 44, 45; 74, 75; 84, 85; 94, 95; 104, 105; 114, 115) extending toward said withdrawal end of said body and an expansion device (36, 46) secured to said shell shaped parts at said insertion end of said body to which pressure is applied when increasing a circumference of said body (10, 20, 30, 40, 70, 80, 90, 100, 110).

2. A medical device in accordance with claim 1, wherein said hollow body (10, 20, 30, 40, 70, 80, 90, 100, 110) is essentially shaped as one of a smooth bead and a hollow cylinder with convex faces at said insertion end.

3. A medical device in accordance with claim 1, further comprising an expansion device (36, 46) to which pressure is applied, said expansion device (36) being of an elastic mouldable material, and having a central, coaxial threaded bore (38) into which a partially threaded helmeted cone is screwed.

4. A medical device in accordance with claim 1, further comprising an expansion device (36, 46) to which pressure is applied, said expanding device (46) being manufactured of elastic mouldable material and having a central, coaxial threaded bore (48), a protruding end of a partially threaded cone having a helmet (49) located at said insertion end of said hollow body (40) with which said helmet (49) makes tight contact.

5. A medical device in accordance with claim 1, wherein said hollow body (30, 40, 70, 80, 90, 100, 110) is axially symmetric.

6. A medical device in accordance with claim 1, wherein said cutting edge has a corrugated pattern.

7. A medical device in accordance with claim 1, wherein said elongated withdrawal device (8) within said hollow body (20) and is connected to said hollow body (20) with an adjustable expander (24) which in turn exerts pressure on parts of said hollow body (20), forcing said parts apart.

8. A medical device in accordance with claim 1, wherein an elastic mouldable expanding device, (76, 86, 96, 106, 116) is connected to said elongated withdrawal device (8), having a tube form, and in turn is connected to a pressure medium so that said circumference of said hollow body (70, 80, 90, 100, 110) can be adjusted by said expanding device (76, 86, 96, 106, 116).

9. A medical device in accordance with claim 1, wherein within said hollow body (30, 40, 70, 80, 90, 100, 110) elastic, mouldable oblique blocking bodies (82, 83; 92, 93; 102, 103) are mounted, pointing inward, to retain dislodged plaque deposits within said hollow body (80, 90, 100, 110).

10. A medical device in accordance with claim 1 wherein said insertion end of said hollow body (100) is equipped with a guiding catheter (108) which penetrates obstructions in the vessel.

11. A medical device in accordance with claim 1, wherein a guiding body (118) is attached to said elongated withdrawal device (8), and is located proximate said cutting edge (111) and guides said hollow body (100) to a catheter opening.

12. A medical device in accordance with claim 1, wherein a guiding body (118) has a form of a drop with an outer diameter that is less than an outer diameter of said hollow body (110).

13. A medical device in accordance with claim 1, wherein said hollow body (80, 90, 100, 110) and said elongated withdrawal device (8) are of electrical conducting materials and the whole said hollow body up to said cutting edge (81, 91, 101, 111) is coated with insulation material.

14. A medical device in accordance with claim 1 wherein said body (10, 20, 30, 40, 70, 80, 90, 100, 110) is hollow and surrounds a portion of said elongated withdrawal device (8) with said cutting element (11, 21, 31, 41) and said elongated withdrawal device (8) can be securely attached to said insertion end (12, 22, 32, 42) of said body (10, 20, 30, 40, 70, 80, 90, 100, 110).

15. A medical device in accordance with claim 14, wherein said body (10, 20, 30, 40, 70, 80, 90, 100, 110) is essentially shaped as one of a smooth bead and a hollow cylinder with convex faces at said insertion end.

16. A medical device in accordance with claim 15, wherein said hollow body (30, 40, 70, 80, 90, 100, 110) comprises a threaded bore (38, 48) at said insertion end to which a threaded end (37, 47) of said withdrawal device (8) is securely threaded.

17. A medical device in accordance with claim 16, wherein said expansion device (36) is of an elastic mouldable material, and has a central, coaxial threaded bore (38) into which a partially threaded helmeted cone is screwed.

18. A medical device in accordance with claim 16, wherein said expansion device (46) is manufactured of elastic mouldable material and has a central, coaxial threaded bore (48), and a protruding end of a partially threaded cone has a helmet (49) located at an insertion end of said hollow body (40) with which the said helmet (49) makes tight contact.

19. A medical device in accordance with claim 18, wherein said hollow body (30, 40, 70, 80, 90, 100, 110) is axially symmetric.

20. A medical device in accordance with claim 19, wherein said cutting edge has a corrugated pattern.

21. A medical device in accordance with claim 20, wherein said elongated withdrawal device (8) lays within said hollow body (20) and is connected to said hollow body (20) with an adjustable expander (24) which in turn exerts pressure on parts of said hollow body (20), forcing said parts apart and against the arterial wall.

22. A medical device in accordance with claim 21, wherein said elastic mouldable expansion device (76, 86, 96, 106, 116) is connected to said elongated withdrawal device (8), having a tube form, and in turn is connected to a pressure medium so that said circumference of said body (70, 80, 90, 100, 110) can be adjusted by said expansion device (76, 86, 96, 106, 116).

23. A medical device in accordance with claim 22, wherein within said hollow body (30, 40, 70, 80, 90, 100, 110) elastic, mouldable oblique blocking bodies (82, 83; 92, 93; 102, 103) are mounted, pointing inwards, to retain dislodged plaque deposits within said hollow body (80, 90, 100, 110).

24. A medical device in accordance with claim 23, wherein said blocking bodies (82, 83; 92, 93; 102, 103; 112, 113) are spring plates.

25. A medical device in accordance with claim 23, wherein said blocking bodies (92, 93) are parts of an introductory chamber (98) with a retaining projection which is fitted to said hollow body (90).

26. A medical device in accordance with claim 24, wherein said blocking bodies (92, 93) are parts of an introductory chamber (98) with a retaining projection which is fitted to said hollow body (90).

27. A medical device in accordance with claim 26, wherein said insertion end of said hollow body (100) is equipped with a guiding catheter (108) which penetrates obstructions in the vessel.

28. A medical device in accordance with claim 27, wherein a guiding body (118) is attached to said elongated withdrawal device (8), and is located proximate to said withdrawal end of said hollow body and guides said hollow body (100) to a catheter opening.

29. A medical device in accordance with claim 28, wherein said guiding body (118) has a form of a drop with an outer diameter that is less than an outer diameter of the hollow body (110).

30. A medical device in accordance with claim 29, wherein said body (80, 90, 100, 110) and said hollow elongated withdrawal device (8) are of electrical conducting materials and the whole said hollow body up to said cutting edge (81, 91, 101, 111) is coated with an insulation material.

* * * * *